(12) United States Patent
Purekar et al.

(10) Patent No.: US 8,285,495 B2
(45) Date of Patent: Oct. 9, 2012

(54) CORROSION INSPECTION AND MONITORING SYSTEM

(75) Inventors: Ashish S. Purekar, Silver Spring, MD (US); Norman Mark Wereley, Potomac, MD (US); Peter Che-Hung Chen, Clarksville, MD (US)

(73) Assignees: Techno-Sciences, Inc, Calverton, MD (US); University of Maryland, College Park, College Park, MD (US)

(*) Notice: Subject to any disclaimer, the term of this patent is extended or adjusted under 35 U.S.C. 154(b) by 260 days.

(21) Appl. No.: 12/770,206

(22) Filed: Apr. 29, 2010

(65) Prior Publication Data

US 2010/0312493 A1    Dec. 9, 2010

Related U.S. Application Data

(60) Provisional application No. 61/214,846, filed on Apr. 29, 2009.

(51) Int. Cl.
*G01B 5/28* (2006.01)
*G01M 1/14* (2006.01)
*G01R 29/22* (2006.01)

(52) U.S. Cl. ............ 702/39; 73/1.82; 324/727

(58) Field of Classification Search .......... 702/39, 702/34–36, 41–43, 56–57, 64–67, 70, 72, 702/75–77, 81, 84, 127, 159, 168, 170–171, 702/182–183, 185, 189–191, 199; 73/1.82, 73/570, 577, 583–584, 594, 596, 598–600, 73/632, 645–646, 649, 657, 760, 763, 768, 73/774–775, 781, 783, 786–787, 799, 802, 73/804; 324/602–603, 605, 609, 616–620, 324/622, 639, 654, 658–660, 676, 727
See application file for complete search history.

(56) References Cited

U.S. PATENT DOCUMENTS

| | | | |
|---|---|---|---|
| 5,139,627 A | 8/1992 | Eden | |
| 5,306,414 A | 4/1994 | Glass | |
| 5,367,583 A | 11/1994 | Sirkis | |
| 6,006,163 A | 12/1999 | Lichtenwalner | |
| 6,799,466 B2 | 10/2004 | Chinn | |
| 2006/0081071 A1* | 4/2006 | Kessler et al. | 73/862.391 |
| 2007/0012111 A1* | 1/2007 | Kim | 73/594 |

OTHER PUBLICATIONS

Purekar, A., Piezoelectric Phased Array Acousto-Ultrasonic Interrogation of Damage in Thin Plates, 2006, Ph. D. Dissertation, Department of Aerospace Engineering, University of Maryland, 243 pp.*

* cited by examiner

*Primary Examiner* — Toan M Le
(74) *Attorney, Agent, or Firm* — Ober, Kaler, Grimes & Shriver; Royal W. Craig (57) ABSTRACT

A system for in-situ near-real-time detection and monitoring of corrosion in structures with the ability to directly track the presence and growth of corrosion on a structure by measurement of material loss in the structure attained by analysis of high frequency wave propagation dynamics. The Corrosion Inspection and Monitoring (CIM) system utilizes low-weight in-situ transducers and unique data reduction software for detection and monitoring of corrosion in structural systems in near real-time for corrosion related damage. The CIM system provides a corrosion monitoring and tracking tool that can be deployed in the field with the structural system, and no maintenance personnel are needed for corrosion analysis.

21 Claims, 9 Drawing Sheets

CORROSION INSPECTION AND MONITORING SYSTEM

CROSS-REFERENCE TO RELATED APPLICATION(S)

The present application derives priority from U.S. provisional application Ser. No. 61/214,846 filed 29 Apr. 2009.

BACKGROUND OF THE INVENTION

1. Field of the Invention

The present invention relates to non-destructive testing and evaluation and, more particularly, to a system for in-situ detection and monitoring of corrosion in structures with the ability to directly track the presence and growth of corrosion on a structure by measurement of material loss in the structure.

2. Description of Background

Structural health monitoring systems aim to diagnose flaws in components to prevent catastrophic degradation and failure. The benefit of such a system is the ability to determine the need for replacement of a structural component. This need often arises as a result of corrosion damage.

Corrosion damage is of significant concern across all engineering fields. Corrosion damage to vehicle components (aerospace, naval, and land vehicles) is the predominant form of damage and limits the useful life of structures and their components. Corrosion consists of an electrochemical interaction between materials which gradually degrades the material over time. Structural components which undergo the corrosive process lose material and, as a result, exhibit lowered structural integrity. The loss of structural integrity increases the likelihood of failure of the part. Coatings exist which aim to prevent corrosion by providing a barrier for the electrochemical interaction involved in the corrosive process. However, the best outcome when using coating techniques is a delay in the onset of corrosive damage on systems in the field. Wear and tear experienced by systems in the field reduces the efficacy of such coatings. Thus corrosion monitoring systems are still necessary for fielded systems.

Significant effort, in the form of manpower and monetary resources, is required for diagnosing corrosion damage and replacing parts. Since corrosion damage is closely linked to operational environment and use, conventional predictions of corrosion damage to structural components are speculative. Therefore, there is a significant industrial demand for a more reliable diagnostic system for corrosion monitoring and growth tracking, since this would save significant manpower and costs associated with corrosion damage. Such a corrosion monitoring system would reduce the costs associated with maintenance and also reduce total life cycle costs. These savings are significant, especially when extended to a fleet of systems such as air or ground vehicles.

Existing corrosion monitoring techniques can be classified into three main categories. The first category consists of sensor implementations that rely on sacrificial materials that corrode along with the base substructure on which the sensor is mounted. For example, U.S. Pat. No. 5,367,583 describes a technique based on fiber optics which uses a sacrificial element. The second category consists of sensors and techniques that monitor low level electric potentials and electric currents which indicate the presence of a corrosion process. For example, U.S. Pat. No. 5,139,627 describes a sensor system which measures the electric current related to corrosion. The third category is based on sensor techniques which measure the chemical properties of the environment for factors conducive to corrosion formation. As an example, U.S. Pat. No. 5,306,414 describes a technique that measures chemical species in the environment.

Other forms of non-destructive testing and evaluation have been used in other contexts. For example, techniques based on in-situ smart materials for structures have been used for health monitoring. In-situ sensors and actuators are used to excite a structure using high frequency vibrations and advanced algorithms are used for damage detection. For example, U.S. Pat. No. 6,006,163 describes a system using piezoelectric transducers and broadband excitation for damage detection of structures. U.S. Pat. No. 6,799,466 describes a system using electromagnetic acoustic transducers for pipeline monitoring.

To the best of the present inventor's knowledge, there have been no known efforts at corrosion monitoring by direct monitoring of the structure as opposed to the use of sacrificial elements, measurement of electric potentials and currents, or environmental properties conducive to corrosion. It would be greatly advantageous to provide a system with the ability to directly track the presence and growth of corrosion on a structural system by relying on guided waves to directly measure material loss, rather than relying on conventional methods which have inherent drawbacks.

Other features, advantages and characteristics of the present invention will become apparent after the following detailed description.

SUMMARY OF THE INVENTION

Accordingly, it is an object of the present invention to provide a Corrosion Inspection and Monitoring (CIM) system that is able to detect, localize, and estimate the severity of damage due to corrosion in a structure or structural component by excitation of high frequency guided waves for measurement of material loss due to corrosion.

It is another object to provide a sensing methodology for implementing corrosion monitoring and growth tracking in structural components using a non-destructive testing system for thin walled structures.

It is a further object to provide a data analysis algorithm for corrosion growth tracking based on sensor signals acquired from in-situ transducers.

It is a further object to provide a corrosion monitoring method with the ability to scale up for large areas.

It is a further object to provide a corrosion monitoring and growth tracking methodology for arbitrary structural configurations.

In accordance with the foregoing objects, the present invention is a system for in-situ near-real-time detection and monitoring of corrosion in structures with the ability to directly track the presence and growth of corrosion on a structure by measurement of material loss in the structure. The Corrosion Inspection and Monitoring (CIM) system of the present invention utilizes in-situ transducers and unique data reduction algorithms for detection and monitoring of corrosion in structural systems. The CIM system has the ability to provide near real-time status of a structural component for corrosion related damage. The CIM system directly measures material loss in the structure.

The CIM system uses low weight, in-situ transducers to minimize the added weight to a structural system. The in-situ nature of the CIM system allows for a structural system to be fielded with transducers mounted. With the use of data acquisition and signal analysis tools, the CIM system can provide a corrosion monitoring and tracking tool which is fielded with the structural system. The CIM system does not require maintenance personnel for corrosion analysis.

Another benefit of the system is the ability to be isolated from other operating components related to the structural system. The transducers of the present invention utilize high frequency wave propagation dynamics of structures for corrosion growth tracking. By using high frequency dynamics, the CIM system is not affected by ambient vibrations due to machinery operations such as pumps or engines.

The CIM system can be integrated into damage inspection schemes using distributed in-situ transducers which examine structural systems for damage related to fatigue related crack formation. The CIM system can form a part of an overall structural health monitoring system for aerospace, mechanical, industrial, and civil structural systems. Specifically, the invention may be applied to aerospace systems (such as rotary wing and fixed wing platforms), mechanical systems (such as ground vehicles and marine vessels), industrial systems (such as manufacturing plants and machinery), and civil systems (such as bridges and buildings).

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

The present invention is a system inclusive of method and apparatus for in-situ near-real-time detection and monitoring of corrosion in structures by direct measurement of material loss in the structure, and corresponding analysis of the presence and growth of corrosion on the structure, to provide near real-time status of the structure for corrosion related damage.

The method comprises a non-destructive evaluation technique for determining the presence of corrosion damage and monitoring corrosion growth for a structural component using in-situ active elements. This technique is based on a guided wave approach where high frequency vibrations in the form of wave packets are imparted onto the structure using active materials, and are sensed on the structure using active materials. A wave packet is herein defined as a short burst or envelope of waves that travel as a unit. For thin-walled structural components, Lamb waves are used to describe the propagation of wave modes through the structure. Lamb waves propagate in solid media. They are elastic waves whose particle motion lies in the plane defined by the thin-walled structural component and the direction of wave propagation. For thicker components, Rayleigh waves and Love waves are used to describe wave motion. Love waves have transverse motion (movement is perpendicular to the direction of travel, like light waves), whereas Rayleigh waves have both longitudinal (movement parallel to the direction of travel, like sound waves) and transverse motion. The present invention uses the properties of these guided waves and their interaction with damage for a direct measurement of corrosion in the structural component. It should be understood that the present discussion is a description of an example embodiment and is not intended as limiting the application of the present invention. Features illustrated or described as part of an embodiment may be used in another embodiment without departing from the scope and spirit of the invention. It is understood that the present invention encompasses such modifications and variations.

Figure 1:
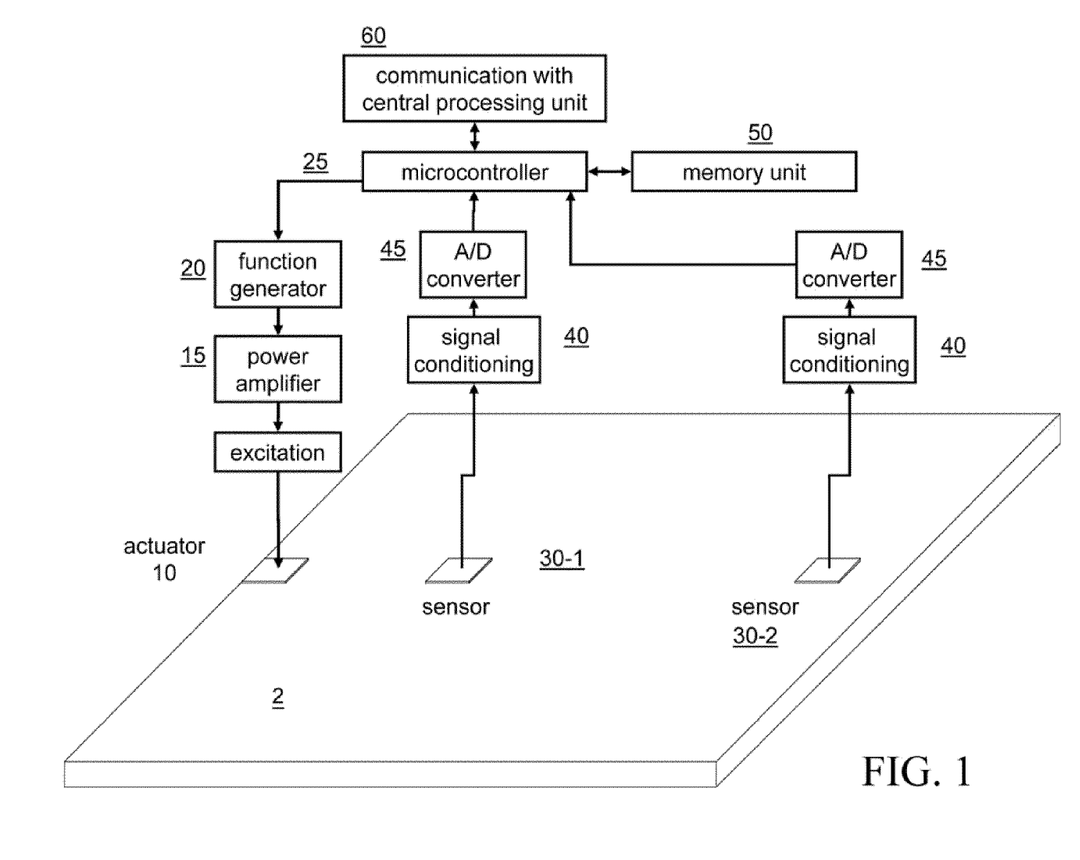
FIG. 1 is a schematic block diagram of components of the CIM system on a panel structure according to an exemplary embodiment.

FIG. 1 is a schematic block diagram of a Corrosion Inspection and Monitoring (CIM) system for general panel type structures according to an embodiment of the present invention, here shown mounted on a flat panel structure 2. The CIM system includes an actuator element 10 mounted on the panel structure 2 to excite the panel structure 2 using high frequency tone bursts. The actuator element 10 is connected to a power amplifier 15 which conditions the excitation signal provided by a function generator unit 20. The function generator unit 20 is programmed through a microcontroller unit 25. The function generator unit 20 may be any suitable commercially-available function generator capable of remote programming (by microcontroller unit 25), including triggered delivery of a tone burst or a gated burst (an excitation signal turned on and off by a gate signal from microcontroller unit 25).

Sensor element(s) 30-1, 30-2 . . . n are mounted on the panel 2 at various locations and are used to convert the mechanical deformations due to wave propagation into voltage signals through use of signal conditioning electronics 40. An analog to digital converter 45 is used for digitizing the signals to be read by the microcontroller unit 25 acting as a data acquisition unit. The microcontroller unit 25 interfaces with a memory unit 50 to store information, and may interface with a remote central processing unit or computer through a communication unit 60.

In operation, narrow bandwidth high-frequency tone burst excitation signals are sent by the function generator 20 through the power amplifier 15 to the actuator element 10, which imparts the tone burst excitation signals in periodic wave packets to generate a mechanical disturbance into the platform structure 2. Each wave packet comprises a ashort burst or envelope of wave action that travels as a unit. Each wave packet generated by the actuator element 10 propagates through the structure 2 from the actuator 10 location outward. The wave packet passes through the locations where sensor elements 30-1, 30-2 are mounted. The properties of the wave packet are dependent on the type of wave mode excited by the actuator 10. When corrosion damage is present in the structure, the wave packets are modified based on the position and extent of corrosion damage. In the preferred embodiment of the CIM system, a baseline case is evaluated where the panel 2 is considered to be undamaged, and this is used for comparison.

Figure 2:
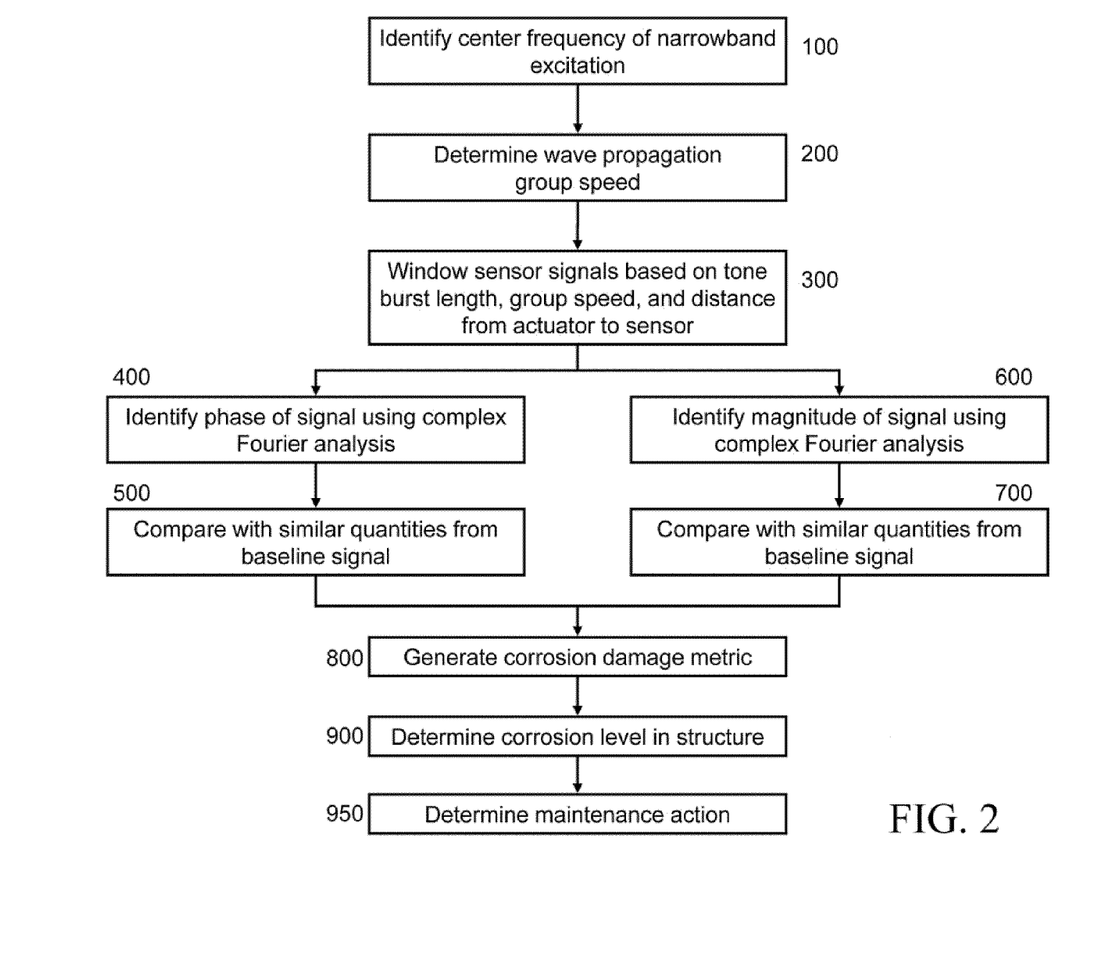
FIG. 2 is a schematic block diagram of processing logic for corrosion monitoring according to an embodiment of the method of the present invention.
Figure 3:
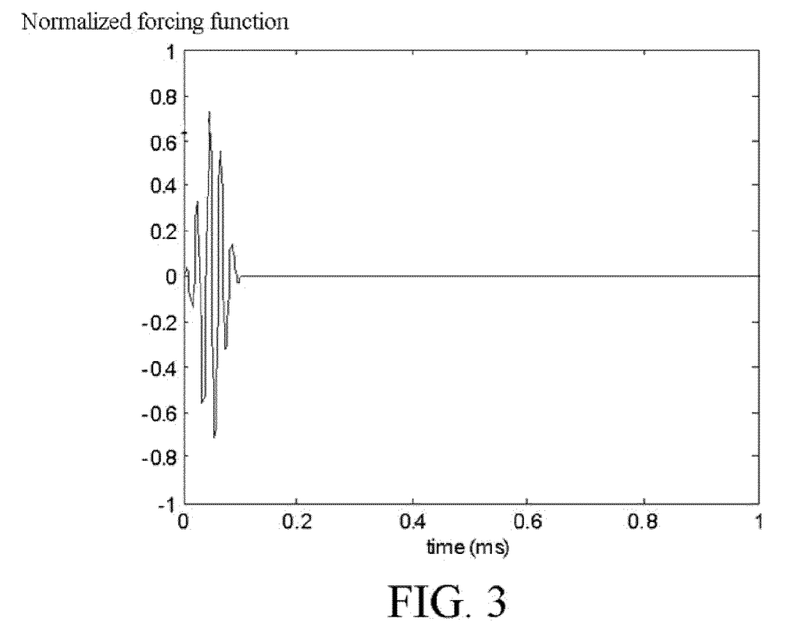
FIG. 3 is an exemplary narrowband excitation signal using a short duration pulse (50 kHz center frequency).
Figure 4:
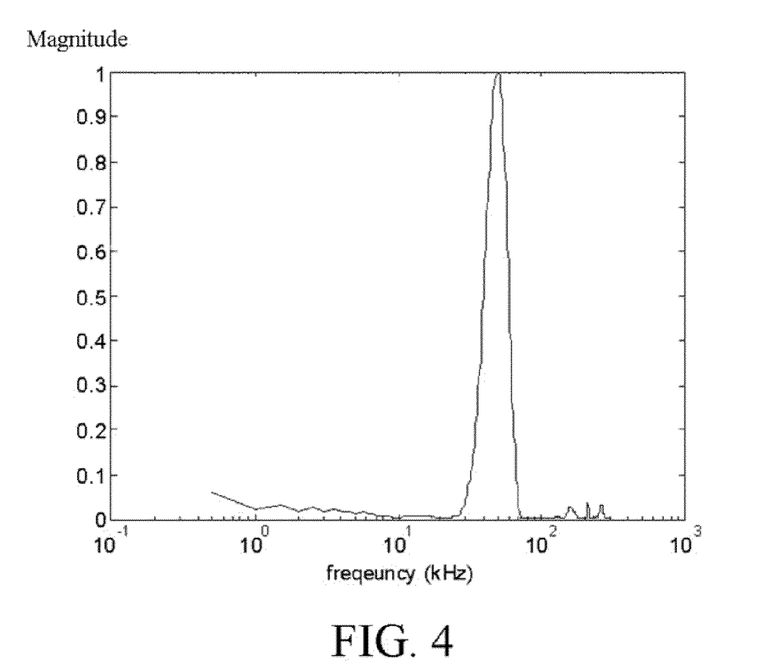
FIG. 4 is a frequency spectrum of exemplary narrowband, short duration excitation signal.

FIG. 2 is a schematic block diagram of processing logic for corrosion monitoring in accordance with an embodiment of the method of the present invention. Given narrowband tone burst excitation sent by the function generator 20 through the power amplifier 15 to the actuator element 10, signals are gathered from one of the sensor elements 30-1, 30-2 and are analyzed based on the block diagram of FIG. 2. For example, we may assume that an excitation signal composed of a narrowband signal, f(t), is used to excite the structure using a short duration pulse at a frequency of excitation ω. An example of a suitable excitation signal is shown in FIG. 3 along with the corresponding frequency spectrum in FIG. 4. The duration of the excitation signal is assigned to Δt. Other excitation functions may be constructed and used in a similar manner.

At step 100, the analysis method begins by identifying a center frequency of the signals gathered from the sensor element 30-1 or 30-2. The frequency of excitation w of the narrowband excitation is determined from the testing conditions.

At step 200, a wave propagation group speed of the signals gathered from a sensor element 30-1 or 30-2 is determined. An approximation of the wave propagation group speed is determined based on simplified model information, empirical studies, or advanced analysis techniques. For a simple panel structure at low frequencies, the group speed relation is described by $$c_g = 2\frac{\omega}{k} = 2\sqrt{\omega}\sqrt[4]{\frac{D}{\rho t}} \tag{1}$$

Where ω is the frequency of excitation, k is the Wavenumber corresponding to the given frequency, D is the structural rigidity, ρ is the density, and t is the thickness of the panel. Higher fidelity estimates of the group speed based on advanced mathematical models may be used as well.

At step 300, the sensor signals are sorted and separately windowed based on tone, burst length, group speed, and distance from actuator 10 to sensor 30-1 or 30-2. The sensor signals are windowed based on the arrival time of the wave packet from the actuator location, described by $$t_c = l/c_g \tag{2}$$

The sensor signals are windowed between $t_1$ and $t_2$ as prescribed below $$t_1 = t_c - \Delta t/2;\ t_2 = t_c + \Delta t/2 \tag{3}$$

Where t is the travel time from the actuator element 10 to sensor element 30-1 or 30-2, and l is the distance from the actuator element 10 to the sensor element 30-1 or 30-2. The signals may be processed using Fourier analysis techniques to extract phase and magnitude information, though one skilled in the art will understand that other analysis techniques may be used as well, including but not limited to Wavelet analysis.

At step 400, the phase of the signal is determined. Using complex Fourier analysis, the Phase information is determined using the following equations $$\phi = \int s_w(t) e^{i\omega_c t} dt \tag{4}$$

$$\theta = \tan^{-1}\left(\frac{\mathrm{Im}(\phi)}{\mathrm{Re}(\phi)}\right) \tag{5}$$

Where $s_w$ is the windowed sensor signal for either undamaged or the undamaged baseline case and $\omega_c$ is the center frequency of the narrowband excitation signal. θ is the phase of the signal. The phase lag between the undamaged state and the corroded state of the structural component is determined using the following.

$$\theta_{dam} = \tan^{-1}\left(\frac{\mathrm{Im}(\phi_{dam}/\phi_{und})}{\mathrm{Re}(\phi_{dam}/\phi_{und})}\right) \tag{6}$$

Where $\theta_{und}$ and $\theta_{dam}$ correspond to undamaged and damaged conditions. The sensor signals corresponding to the undamaged state of the structural component are saved from initial experimentation. The sensor signals corresponding to a corroded state are used to generate $\theta_{dam}$ data.

At step 600, the magnitude of the signal is determined. Using complex Fourier analysis, the magnitude information is found in a similar manner using the $\theta_{und}$ and $\theta_{dam}$ data.

$$e_{dam} = 10 \log(\phi_{dam}/\phi_{und}) \tag{7}$$

At steps 500 and 700, the foregoing phase and magnitude are compared with similar quantities from previously-determined baseline or reference signals.

At step 800, a corrosion damage metric is generated from the comparison data.

At step 900 the actual corrosion level in the structure is calculated using the corrosion damage metric from step 800.

Finally, at step 950, the proper maintenance or remedial action is determined based on the actual corrosion level in the structure calculated at step 900.

Test Results

Figure 5:
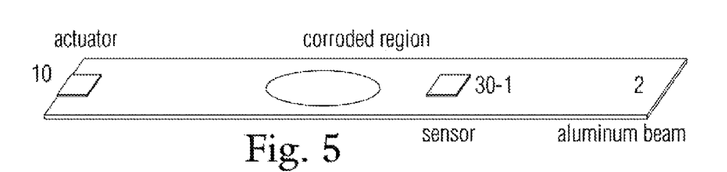
FIG. 5 is a graphic illustration of instrumentation configuration employed in a proof-of-concept experimental laboratory setup of the CIM system according to the present invention.

To test the foregoing system an aluminum beam 2 was equipped with piezoelectric ceramic elements, one serving as actuator 10 and one as sensor 30-1.

FIG. 5 is a perspective drawing of this test setup. A piezoelectric ceramic element was mounted as actuator 10 to the end of aluminum beam 2. A piezoelectric ceramic element was bonded as sensor 30-1 a distance from the actuator element 10. An accelerated corrosive treatment was applied to the region between the actuator element 10 and the sensor element 30-1 to simulate material loss due to corrosive effects.

Figure 6:
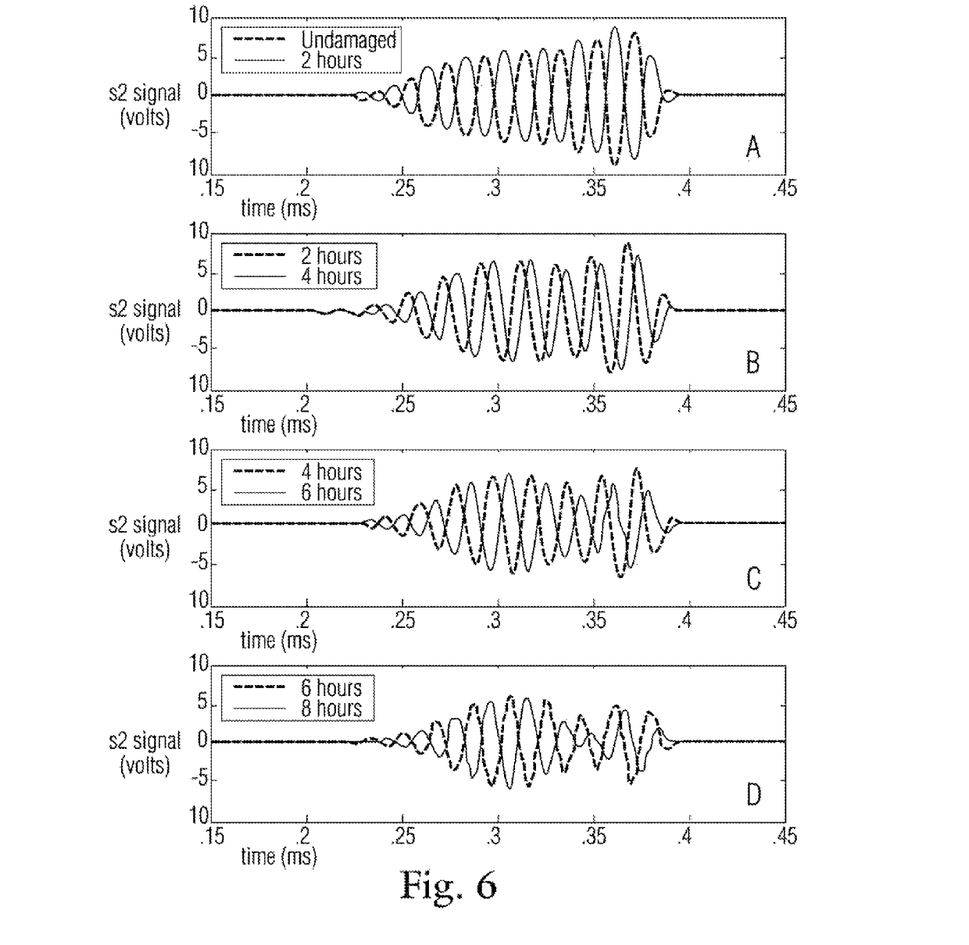
FIG. 6 is a series of graphs depicting the transient response from sensor at 50 kHz excitation of the first actuator/sensor instrumentation configuration employed in the experimental laboratory setup of the CIM system.

The windowed sensor signals returned from sensor element 30-1 are provided in FIGS. 6a, b, c, and d for an excitation frequency of 50 kHz for progressively growing corrosive conditions. The sensor signals show the effect of corrosion on the movement of wave packets. A direct change in phase and magnitude of the signals are observed in the sensor signals. This information is quantified using metrics as described further.

Figure 7:
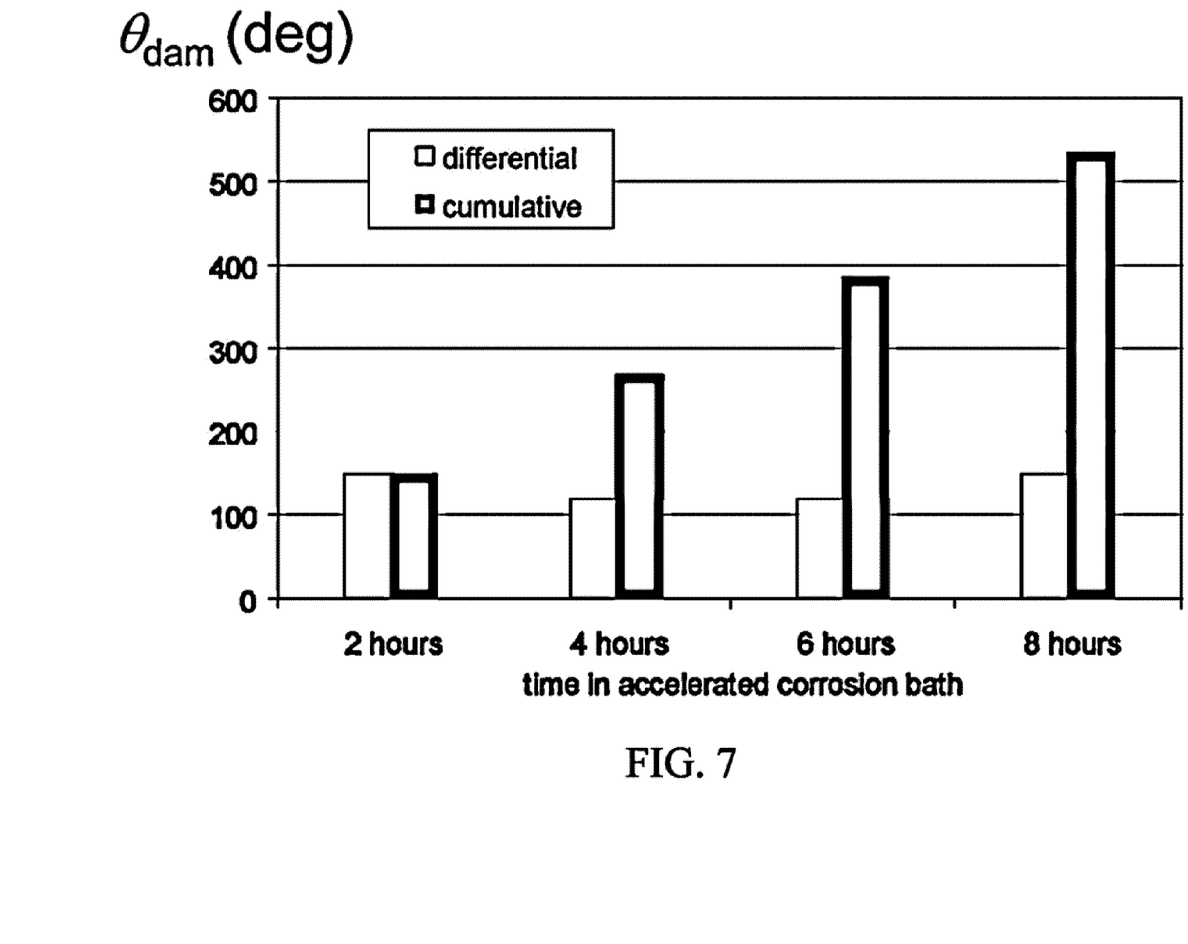
FIG. 7 is a graph depicting the differential and cumulative phase lag from sensor of the first actuator/sensor instrumentation configuration employed in the experimental laboratory setup of the CIM system.
Figure 8:
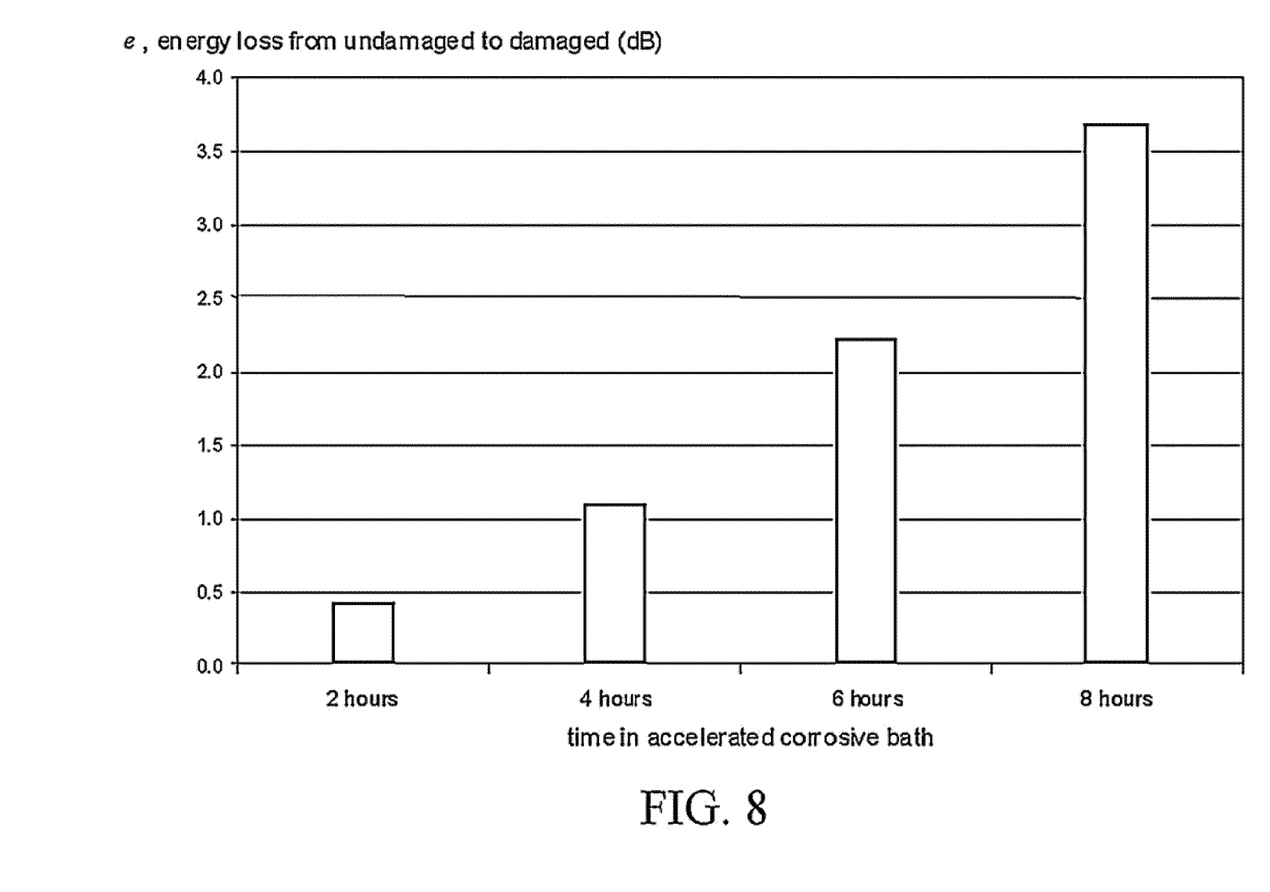
FIG. 8 is a graph depicting the cumulative magnitude loss from sensor of the first actuator/sensor instrumentation configuration employed in the experimental laboratory setup of the CIM system.

The phase lag information $\theta_{dam}$ calculated based on the sensor signals from FIG. 6 are shown in FIG. 7. The differential phase lag information corresponds to change in phase for progressive damaged conditions. The cumulative phase lag information corresponds to total phase lag of the sensor signal for a corroded state compared to the undamaged response. The cumulative phase lag information shows the effect of progressively increasing amounts of corrosion in the proof-of-concept laboratory setup. The increase in phase lag as corrosion increases is due to the effect of material loss on wave propagation. The corroded section becomes thinner do the material loss which causes a loss of speed for the wave packet. The loss of speed causes the wave packet to arrive at a later time when compared to damage of a lesser extent or no damage at all. The change in the energy of the sensors signals is quantified and presented in FIG. 8. An increase in the energy loss is observed as the level of corrosion increases.

Figure 9:
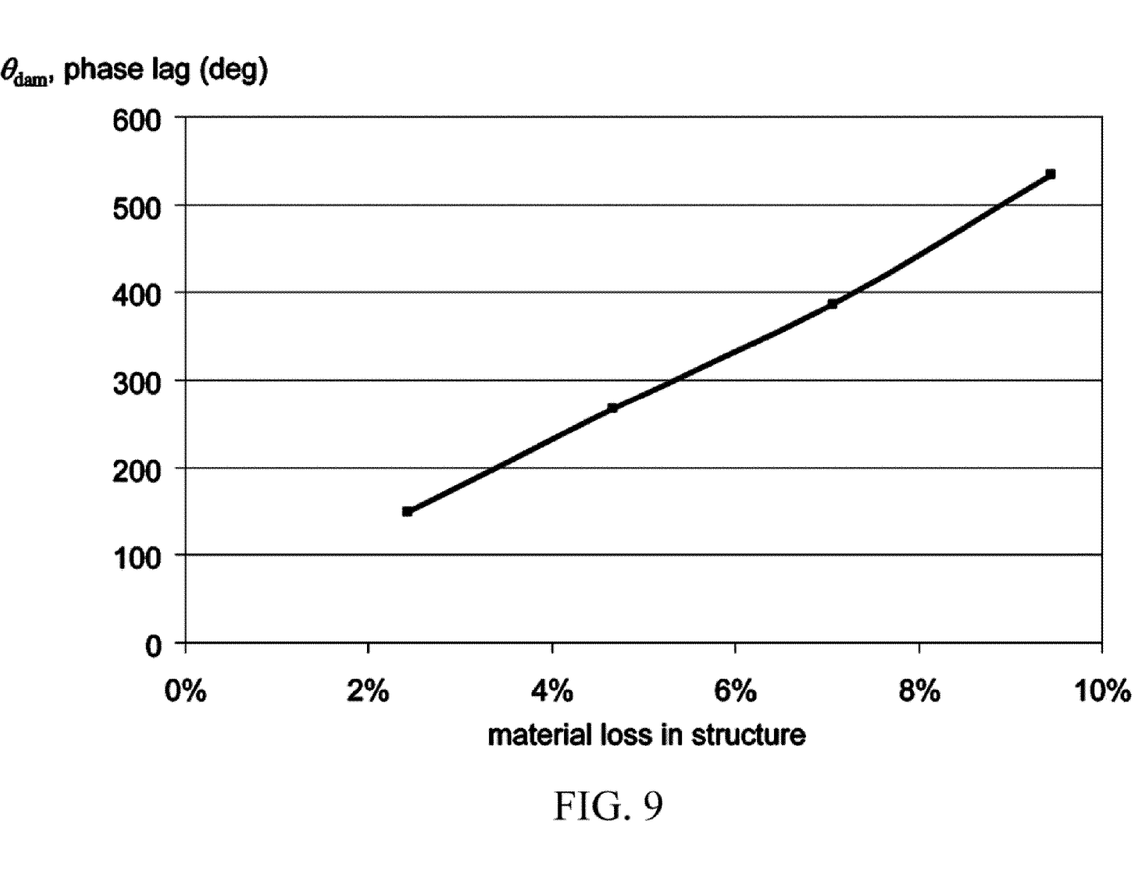
FIG. 9 is a graph depicting the phase lag information versus material loss in the exemplary proof-of-concept laboratory experimentation of the CIM system.

Corrosion damage is commonly described in terms of material loss in the structural component. The beam structure in the exemplary embodiment of the CIM system was weighed between progress corrosion levels and compared to the phase lag information found. FIG. 9 illustrates the graphical results and shows the ability of the CIM system to evaluate corrosion level.

Transducers

Figure 10:
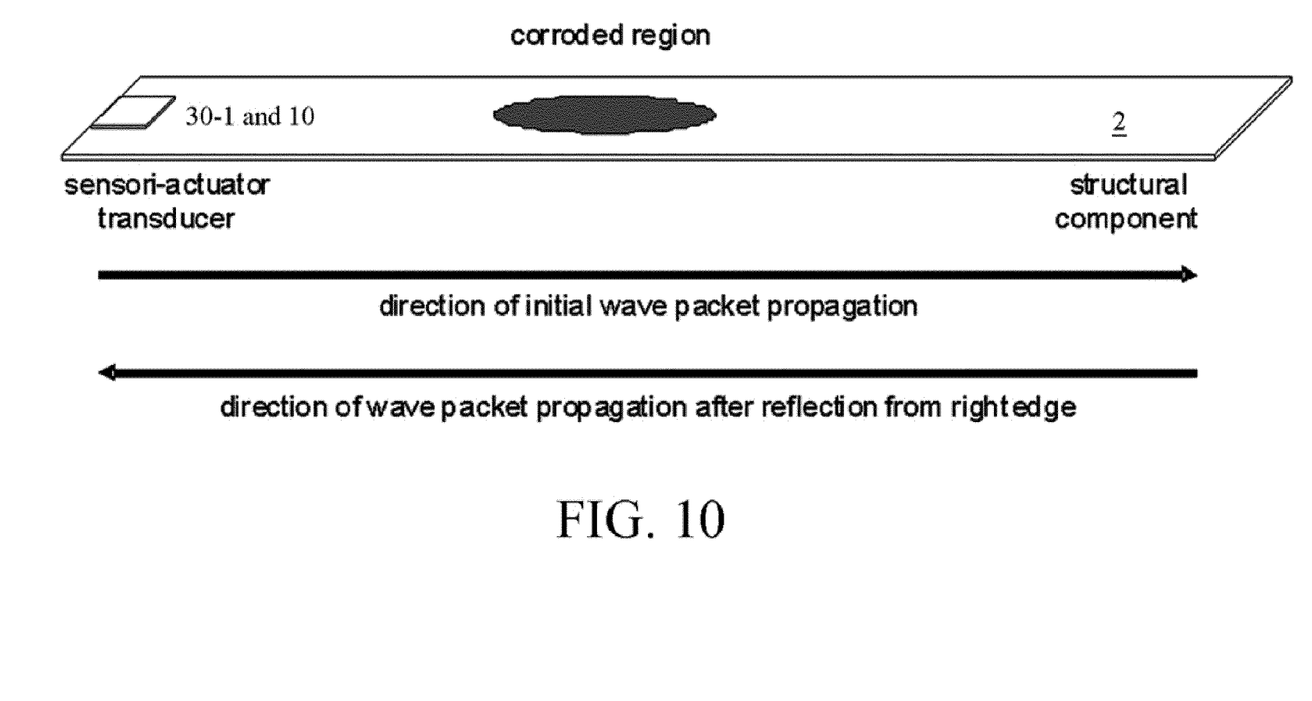
FIG. 10 is an alternate embodiment of CIM system using sensori-actuator transducers for actuation and sensing.

The test configuration described above used piezoelectric materials for transduction. However, the present invention encompasses the use of different types of material for transduction of high frequency wave propagation in the structural member 2. All of piezoelectric materials, piezoceramic, polyvinylidene fluoride (PVDF), piezoelectric crystals, and piezoelectric composite materials are included as potential transducer elements. Piezoceramic materials include, but are not limited to, compositions of $BaTiO_3$, $PbTiO_3$, $Pb[Zr_xTi_{1-x}]O_3$ ($0<x<1$), $KNbO_3$, $LiNbO_3$, $LiTaO_3$, $Na_2WO_3$, $Ba_2NaNb_5O_5$, $Pb_2KNb_5O_{15}$. KNN, and $BiFeO_3$. Piezoelectric crystals include, but are not limited to, $GaPO_4$ and $La_3Ga_5SiO_{14}$. Piezoelectric elements can be used as combined sensors 30-1 . . . n and actuators 10 in the CIM system. The sensori-actuator piezoelectric technology can be used to both excite and sense high frequency wave propagation in structural components. In the case of sensori-actuator technologies, a single element can be used as part of the CIM system. For the exemplary embodiment described previously, a CIM system consisting of a single transducer is shown in FIG. 10. Wave packets travel from the transducer through the beam structure (including the corroded region, if present) and reflect off of the edge and travel back again toward the sensori-actuator element. In this manner, a single sensori-actuator is able to evaluate corrosion over the entire structural configuration.

One skilled in the art will readily understand that alternate sensing and actuation technologies may be used as elements of the CIM system. For sensing, technologies include, but are not limited to, strain gage elements, accelerometers, laser vibrometers, ferro-electric materials (including electrostrictive and piezo-electric) materials, and technologies based on materials exhibiting magnetostrictive (e.g., polycrystalline or single crystal TerFe or GaFe or composites thereof), magnetorheological materials (e.g. any size or shape particles of Fe, Co, or Ni, or alloys thereof, dispersed in a relatively soft matrix e.g. elastomer or polymer), or other material technologies which couple electric or magnetic properties with mechanical deformations. For actuation, technologies include, but are not limited to, ultrasonic transducers and materials exhibiting magnetostrictive properties.

Scaled Structural Configurations

Figure 11:
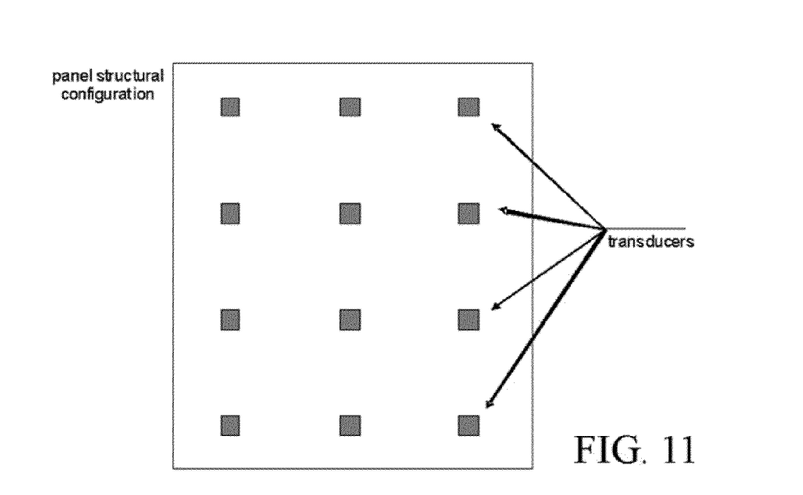
FIG. 11 is an alternate embodiment of CIM system for a panel type structural configuration using a grid distribution.

The CIM system can be scaled based on the structural component of interest. For panel structures, an exemplary embodiment for a CIM system is shown in FIG. 11. A distributed set of transducers 30-1 . . . n are used to evaluate corrosion in the different regions of the panel 2. These sensors 30-1 . . . n can be distributed in spatially regular pattern as shown in FIG. 11, or other patterns including, but not limited to, the regular pattern shown in FIG. 11 with certain transducers missing, spirals, crosses, circles, or random patterns. The algorithm described in the previous sections can be easily adapted for the structural configuration and can be scaled to any arbitrary size configuration. In addition, the algorithms described in the previous section can be reconfigured to accommodate a loss of one or more sensors and/or exciters to optimally detect corrosion damage.

Structural configurations made of metallic and composite structures or combinations thereof may be instrumented using the CIM system. Metallic materials including, but not limited to, aluminum, steel, titanium, their alloys, and laminations of dissimilar metallic layers (e.g., laminations of aluminum and titanium) may be considered. It is envisaged that this system can be used to inspect corrosion in composite materials. Structures made of composite materials include fiber reinforced laminates, particle composites, and flake composites. Materials used for composite structures include, but are not limited to, carbon fiber, glass fiber, graphite fiber, with resin or polymer matrix (e.g. composites composed of graphite, Kevlar, E-glass, S-glass etc. fibers in a polymer or resin matrix), metal matrix composites, and ceramic matrix composites (e.g. carbon-carbon). Laminates consisting of combinations of metallic layers and composite layers (for example, Glass Reinforced (GLARE) Fiber Metal Laminate (FML) composites or Titanium-Graphite composites) could also be monitored using the CIM system. It is expected that the CIM system will be particularly adept at detecting subsurface crack and corrosion damage in these fiber-metal laminates.

Figure 12:
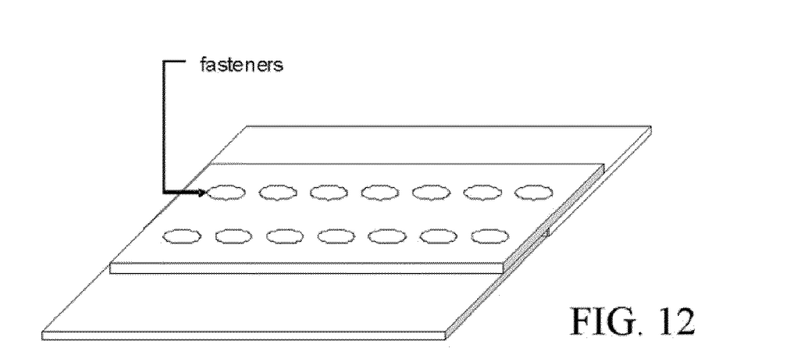
FIG. 12 is an alternate embodiment of the CIM system for a jointed panel using fasteners such as rivets or bolts with or without adhesive.
Figure 13:
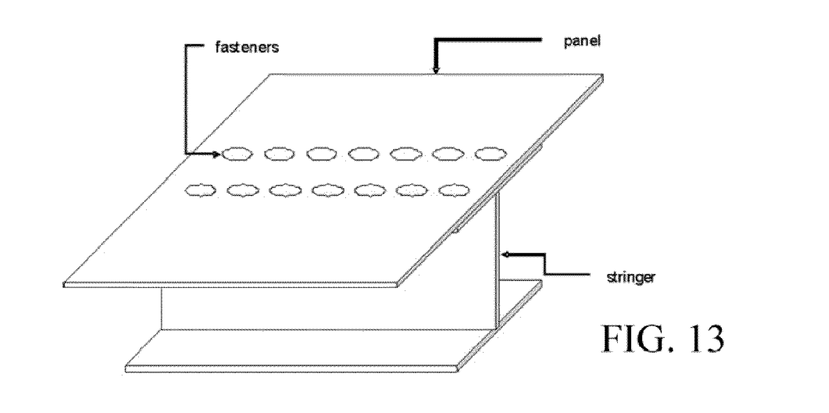
FIG. 13 is an alternate embodiment of a CIM system for a panel stringer assembly.

Examples of complex structural configurations which may be examined using the CIM system include, but are not limited to configurations such as joints using a multitude of panels, shown in FIG. 12, or panel/stringer assemblies, shown in FIG. 13. The configurations may be assembled using fasteners 40-1 . . . n such as bolts or rivets or adhesive backing and can include dissimilar materials.

In all the above-described embodiments, the CIM system is able to detect, localize, and estimate the severity of damage due to corrosion in a structure or structural component by excitation of high frequency guided waves and measurement of material loss due to corrosion. The sensing system is completely non-destructive and well-suited for testing thin walled structures. Moreover, the data analysis can monitor and track corrosion growth based on sensor signals acquired from in-situ transducers. The system can be scale up or down for larger or smaller areas, as desired, and is suitable for arbitrary structural configurations.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

What is claimed is:

1. A corrosion inspection and monitoring (CIM) system for detection and monitoring of corrosion in a structure by direct measurement of material loss in the structure, comprising:
   a microcontroller including memory;
   a function generator in communication with said microcontroller for generating a high-frequency tone burst excitation signal;
   a power amplifier connected to said function generator for conditioning the high-frequency tone burst excitation signal;
   an actuator connected to said power amplifier and in contact with said structure for imparting each said conditioned high-frequency tone burst excitation signal into said structure as a wave packet to generate a mechanical disturbance into the structure;
   a plurality of sensors mounted on said structure and spatially-displaced from said actuator for sensing mechanical deformation in said structure due to said wave packet wave propagation and for converting said mechanical deformation into voltage feedback signals;
   an analog-to-digital converter connected between said plurality of sensors and said microcontroller for digitizing the feedback signals and transmitting the digitized signals to the microcontroller; and
   software stored in said microcontroller memory and configured to execute instructions for initiating said function generator to generate said high-frequency tone burst excitation signal through said power amplifier and actuator imparting a wave packet vibration to said structure, to cause said analog-to-digital converter to digitize feedback signals obtained at each of said plurality of sensors as a result of propagation of said wave packet vibration through said structure, to extract differential phase information from the digitized feedback signals quantifying a differential phase shift of said wave-packet at one or more of said plurality of sensors as a result of propagation of said wave packet vibration through said structure, to repeat the foregoing steps over a prolonged period of time and in each instance storing said differential phase information, to calculate a cumulative differential phase shift over said prolonged period of time, and for correlating said cumulative phase shift over said prolonged period of time with material loss from progressing corrosion damage in said structure.

2. The CIM system of claim 1, wherein said plurality of sensors each further comprise a piezoelectric sensor element.

3. The CIM system of claim 1, wherein each said piezoelectric sensor element comprises a sensori-actuator piezoelectric element.

4. The CIM system of claim 3, wherein said actuator comprises a sensori-actuator piezoelectric element.

5. The CIM system of claim 1, wherein said plurality of sensors each further comprise a magnetostrictive sensor element.

6. The CIM system of claim 5, wherein said actuator comprises a magnetostrictive element.

7. The CIM system of claim 1, further comprising a multiplexer for selective reading of any one of said plurality of sensor elements.

8. A computerized method for detection and monitoring of corrosion in a structure by direct measurement of material loss in the structure, comprising the steps of:
   a microcontroller programming a function generator to generate a high-frequency tone burst excitation signal;
   amplifying said high-frequency tone burst excitation signal at a power amplifier;
   transmitting said amplified high-frequency tone burst excitation signal to an actuator in contact with said structure and thereby imparting said amplified high-frequency tone burst excitation signal as a wave packet vibration into the structure;
   sensing said wave packet vibration propagation at a plurality of sensors mounted on said structure, and converting the wave packet vibration sensed at each of said plurality of sensors into feedback signals;
   digitizing the feedback signals at an analog-to-digital converter;
   extracting one of differential phase or differential magnitude information from the digitized feedback signals, said differential phase information quantifying a differential phase shift of said wave-packet as a result of propagation of said wave packet vibration through said structure, and said differential magnitude information quantifying a differential magnitude change of said wave-packet as a result of propagation of said wave packet vibration through said structure from the digitized feedback signals;
   storing said extracted phase differential or magnitude information over a prolonged period of time in computer memory;
   using a computer to calculate one of cumulative differential phase or cumulative differential magnitude information over said prolonged period of time from said stored phase differential or magnitude information, and
   using said computer to correlate said calculated cumulative differential phase or cumulative differential magnitude information with material loss caused by progressing corrosion damage in said structure.

9. The method of claim 8, wherein said step of extracting one of differential phase or differential magnitude information from the digitized feedback signals further comprises extracting differential phase information by the substeps of,
   identifying a center frequency of the digitized feedback signals,
   determining wave propagation group speed of the digitized feedback signals, and
   processing said digitized feedback signals to determine differential phase.

10. The method of claim 9, wherein said substep of processing said digitized feedback signals to determine differential magnitude information further comprises applying complex Fourier analysis.

11. The method of claim 9, wherein said substep of processing said digitized feedback signals to determine differential phase further comprises applying complex Wavelet analysis.

12. The method of claim 8, wherein said step of using said computer to correlate said calculated cumulative differential phase or cumulative differential magnitude information with corrosion damage in said structure further comprises comparing said cumulative differential phase information with baseline reference data.

13. The method of claim 12, wherein said step of using said computer to correlate said calculated cumulative differential phase or cumulative differential magnitude information further comprises calculating an actual corrosion level in the structure.

14. A corrosion inspection and monitoring (CIM) system for detection and monitoring of corrosion in a structure by direct measurement of material loss in the structure, comprising:
- a microcontroller including memory;
- a function generator in communication with said microcontroller for generating an excitation signal;
- an amplifier connected to said function generator for amplifying the excitation signal;
- an actuator connected to said amplifier and in contact with said structure for imparting said excitation signal into said structure as a wave packet to generate a mechanical disturbance into the structure;
- at least one sensor mounted on said structure for sensing mechanical deformation in said structure due to said wave packet wave propagation, and for generating a feedback signal there from; and
- software stored in said microcontroller memory configured to execute instructions for initiating said function generator to generate said high-frequency tone burst excitation signal through said power amplifier and actuator imparting a wave packet vibration to said structure, to cause said analog-to-digital converter to digitize feedback signals obtained at each of said plurality of sensors as a result of propagation of said wave packet vibration through said structure, to extract differential magnitude information from the digitized feedback signals quantifying a differential magnitude of said wave-packet at one or more of said plurality of sensors as a result of propagation of said wave packet vibration through said structure, to repeat the foregoing steps over a prolonged period of time and in each instance storing said differential magnitude information, to calculate a cumulative differential magnitude over said prolonged period of time, and for correlating said cumulative differential magnitude over said prolonged period of time with material loss from progressing corrosion damage in said structure.

15. The CIM system of claim 14, wherein said at least one sensor comprises a plurality of sensors.

16. The CIM system of claim 15, wherein said plurality of sensors comprise at least one piezoelectric sensor element.

17. The CIM system of claim 16, wherein said sensori-actuator piezoelectric element also functions as said actuator.

18. The CIM system of claim 15, wherein said plurality of sensors further comprises at least one magnetostrictive sensor element.

19. The CIM system of claim 18, wherein said magnetostrictive sensor element also functions as said actuator.

20. The CIM system of claim 14, wherein said actuator comprises a magnetostrictive element.

21. The CIM system of claim 14, further comprising a multiplexer for selective reading of any one of said plurality of sensor elements.

* * * * *